US006316027B1

(12) United States Patent
Johnson et al.

(10) Patent No.: US 6,316,027 B1
(45) Date of Patent: Nov. 13, 2001

(54) FAST-DISSOLVING DOSAGE FORMS FOR DOPAMINE AGONISTS

(75) Inventors: Edward Stewart Johnson, Ruscombe; Anthony Clarke, Nettlebed; Richard D. Green, Near Canterbury, all of (GB)

(73) Assignee: R. P. Scherer Technologies, Inc., Paradise Valley, NV (US)

( * ) Notice: Subject to any disclaimer, the term of this patent is extended or adjusted under 35 U.S.C. 154(b) by 0 days.

(21) Appl. No.: 09/666,173

(22) Filed: Sep. 21, 2000

Related U.S. Application Data (6362) Continuation-in-part of application No. 09/011,929, filed as application No. PCT/GB96/02020 on Aug. 16, 1996, now abandoned.

(30) Foreign Application Priority Data

Aug. 18, 1995 (GB) .................................................. 9517062

(51) Int. Cl.[7] .............................. A61K 9/20; A61K 9/14; A61K 31/44; A01N 43/42
(52) U.S. Cl. ......................... 424/464; 424/484; 424/485; 424/486; 424/488; 514/289
(58) Field of Search .................................. 424/464, 484, 424/485, 486, 488; 514/289

(56) References Cited

U.S. PATENT DOCUMENTS

| | | | |
|---|---|---|---|
| 5,073,374 | * 12/1991 | McCarty | 424/435 |
| 5,079,018 | 1/1992 | Ecanow | 426/385 |
| 5,120,549 | 6/1992 | Gole et al. | 424/484 |
| 5,234,957 | * 8/1993 | Mantelle | 514/772.6 |
| 5,298,261 | 3/1994 | Pebley et al. | 424/488 |
| 5,529,789 | * 6/1996 | Lo | 424/473 |
| 5,785,989 | 7/1998 | Stanley et al. | 424/440 |

FOREIGN PATENT DOCUMENTS

| | | |
|---|---|---|
| 3216869 A1 | 5/1982 | (DE) . |
| 0 553 777 A2 | 8/1993 | (EP) . |
| 0 614 659 A2 A3 | 9/1994 | (EP) . |
| 0 630 674 B1 | 3/1999 | (EP) . |
| 77 29663 | 10/1997 | (FR) . |
| WO 91/04757 | 4/1991 | (WO) . |
| WO 92/00735 | 1/1992 | (WO) . |
| WO 93/12769 | 7/1993 | (WO) . |
| WO 94/22445 | 10/1994 | (WO) . |
| WO 96/13251 | 5/1996 | (WO) . |
| WO 97/06786 | 2/1997 | (WO) . |

OTHER PUBLICATIONS

USPTO Trademark Registration No. 0157310; Registered Aug. 1, 1922 for the mark BiSoDol in the name of BiSoDol Co., Inc.

* cited by examiner

*Primary Examiner*—Thurman K. Page
*Assistant Examiner*—Todd D Ware
(74) *Attorney, Agent, or Firm*—Donald O. Nickey; Andrew Rozycki; Daniel Christus

(57) ABSTRACT

In one embodiment, this invention relates to a pharmaceutical composition for oral administration consisting essentially of a gelatin at a concentration up to 5% by weight as a carrier, a solvent, and, as an active ingredient, a dopamine agonist. Alternatively, the invention relates to a composition that takes the form of a solid, unitary fast-dispersing dosage form comprised of a network of an active ingredient after and a water-soluble or water dispersible matrix forming agent or carrier which is inert towards the active ingredient after subliming solvent from the composition in the solid state. The dosage is designed to completely disintegrate within 1 to 30 seconds of being placed in the oral cavity. Compositions which further comprise an anti-emetic and/or an opioid antagonist are also provided herein.

15 Claims, No Drawings

FAST-DISSOLVING DOSAGE FORMS FOR DOPAMINE AGONISTS

RELATED APPLICATIONS

This application is a continuation-in-part application based on U.S. application Ser. No. 09/011,929 filed Feb. 17, 1998, now abandoned, which is a national phase filing of PCT/GB96/02020 (WO 97/06786) with an International Filing Date of Aug. 16, 1996 (16.08.96) which claims priority to GB 9517062.7 filed Aug. 18, 1995 (18.08.95).

FIELD OF THE INVENTION

This invention relates to pharmaceutical compositions, a process for preparing such compositions, the use of such compositions for the treatment and/or evaluation of Parkinson's disease and products and kits for the administration of a dopamine agonist and the co-administration of a dopamine agonist and an anti-emetic and/or opioid antagonist.

BACKGROUND OF THE INVENTION

Parkinson's disease is a progressive neurodegenerative disorder caused by a loss of the cell bodies of dopaminergic neurons from the substantia nigra and degeneration of nerve terminals in the striatum resulting in low levels of dopamine in the substantia nigra and corpus striatum. Parkinson's disease is characterized by chronic, progressive motor dysfunction and its main symptoms are tremor at rest, muscle rigidity and a decrease in the frequency of voluntary movements (hypokinesia) with difficulty in stopping, starting and turning when walking. A persistent tremor is superimposed on hypertonicity of opposing muscle groups and initiation of movements becomes increasingly difficult and slow. In advanced stages, patients' movements become virtually "frozen" and patients are unable to care for themselves. Studies have shown that the symptoms of Parkinson's disease appear when the striatal dopamine content is reduced to 20–40% of normal. As Parkinson's disease is associated with a loss of dopamine from the striatum, it is commonly treated with drugs which replace dopamine, the most commonly used of these being levodopa. Levodopa is converted by dopa decarboxylase into dopamine in the brain and it is this dopamine which exerts a therapeutic effect. However, although levodopa is well absorbed from the small intestine, much of it is inactivated by monoamine oxidase in the wall of the intestine. Also, the plasma half-life of levodopa is short and about 95% of the drug is converted to dopamine in peripheral tissues, where dopa decarboxylase is widespread, with the result that less than 1% enters the brain. Consequently levodopa has to be administered in large and frequent doses. In addition, the production of dopamine in peripheral tissues gives rise to unwanted side effects. Accordingly, levodopa is normally given in combination with other drugs to enhance the effects of levodopa in the brain and minimize its peripheral effects. In particular, levodopa is usually given in combination with a peripheral dopa decarboxylase inhibitor which cannot cross the blood-brain barrier, such as carbidopa, which inhibits the breakdown of levodopa to dopamine outside the brain, thereby reducing peripheral unwanted effects. The inhibitor also ensures that a relatively large amount of an oral dose of levodopa reaches the brain and thus enables the dose of levodopa to be reduced which also reduces peripheral side effects. In addition, a peripheral dopamine antagonist which does not penetrate the blood-brain barrier, such as domperidone, may also be administered to reduce the nausea and vomiting side effects of levodopa.

In addition to the side effects mentioned above, further undesirable effects are associated with the prolonged use of levodopa. In particular, many patients develop involuntary choreiform movements, which are the result of excessive activation of dopamine receptors. These movements usually affect the face and limbs and can become very severe. Such movements disappear if the dose of levodopa is reduced but this causes rigidity to return. Moreover, the margin between the beneficial and the unwanted effect appears to become progressively narrower as the period of levodopa treatment increases. The traditional method of combating this effect is to increase the frequency of administration of levodopa while keeping the overall dose steady. This approach reduces end-of-dose deterioration and diminishes the likelihood of the patient developing the dyskinesias that occurs with high peak doses.

A further complication of long-term levodopa treatment is the development of rapid fluctuations between mobility and immobility for periods ranging from a few minutes to a few hours. This phenomenon is known as the "on-off effect". The "on" state being the preferred state during which nearly normal motor functioning can be attained and the "off" state being characterized by dystonic postures during periods of decreased mobility. Indeed, this effect can produce such an abrupt loss of mobility that the patient may suddenly stop while walking or be unable to rise from a chair in which he had sat down normally a few moments earlier. This effect is commonly unaffected by manipulation of the dose of levodopa and may require treatment with alternative drugs.

In addition to the above long-term side effects of levodopa treatment, it has been found that the effectiveness of levodopa gradually declines with time until it is no longer effective. Also, an increased incidence of malignant melanoma has been observed in patients undergoing treatment with levodopa. Accordingly, the use of levodopa in the treatment of Parkinson's disease is far from ideal.

An alternative approach to the treatment of Parkinson's disease is the use of drugs that mimic the action of dopamine. Such drugs are collectively known as dopamine agonists because they directly stimulate dopamine receptors within the dopamine-deficient nigrostriatal pathway. Unlike levodopa, dopamine agonists do not need to be converted in the brain to active compounds. Also, dopamine agonists are effective in patients in the advanced stages of Parkinson's disease when levodopa is no longer effective because they act directly on the dopamine receptors and are therefore unaffected by the lack of dopamine-producing nerve cells in such patients. However, the action of such dopamine agonists on the dopamine receptors also causes unwanted dopaminergic effects, such as nausea, vomiting and extrapyramidal effects, which can be debilitating and some dopamine agonists, such as apomorphine, are associated with further undesirable side effects, especially when high doses are used, such as sedation, respiratory depression, hypotension, bradycardia, sweating and yawning.

The severity and nature of such side effects can be affected by the mode of administration of the drug. For instance, studies involving apomorphine have investigated a variety of routes for administration of this drug. However, oral administration of apomorphine tablets has required high doses to achieve the necessary therapeutic effect because apomorphine administered by this route undergoes extensive presystemic metabolism in the small intestine and/or liver (the first pass effect). Also, long-term studies involving such oral forms were stopped after 7–10 days due to unexplained rises in blood urea nitrogen. Sub-lingual administration of apomorphine tablets caused severe stomatitis on prolonged use with buccal mucosal ulceration in half the patients treated. Intranasal administration produced transient nasal blockage, burning sensation and swollen nose and lips and, in some of the patients tested, had to be withdrawn because of what was considered to be chemical inflammation of the nasal mucosa. Accordingly, the only satisfactory way of administering apomorphine which avoids high first pass metabolism has been found to be subcutaneous administration and, thus, the only commercially available formulation of apomorphine is a liquid for subcutaneous injection or subcutaneous infusion. Even so, subcutaneous administration does not avoid the normal dopamine agonist side effects, such as nausea and vomiting, and subcutaneous administration, whether by injection or infusion, is not easy to accomplish, particularly by patients whose motor functions are already impaired, and therefore requires training of patients and caregivers. Also, the injection site must be changed every 12 hours to minimize risks of skin discoloration and nodules forming. In view of these problems, it is not surprising that the use of dopamine agonists, such as apomorphine, in the treatment of Parkinson's disease has been largely confined to the treatment of "off" periods caused by levodopa therapy despite the obvious clinical benefits of such drugs over levodopa.

It is apparent from the above that it would be highly desirable from a clinical point of view to find a way of administering dopamine agonists, such as apomorphine, which is easy for the patient to accomplish thereby reducing the need for supervision, and which bypasses first pass metabolism in the liver. According to the present invention there is provided a pharmaceutical composition for oral administration comprising a carrier and, as active ingredient, a dopamine agonist, characterized in that the composition is in the form of a fast-dispersing dosage form designed to release the active ingredient rapidly in the oral cavity.

It has been found that such fast-dispersing dosage forms promote pre-gastric absorption of the active ingredient, that is, absorption of the active ingredient from that part of the alimentary canal prior to the stomach. The term "pre-gastric absorption" thus includes buccal, sublingual, oropharyngeal and oesophageal absorption. Dopamine agonists absorbed by such pre-gastric absorption pass straight into the systemic circulatory system thereby avoiding first pass metabolism in the liver. Accordingly, bioavailability of dopamine agonists absorbed in this way may also be increased. This means that the dose of such dopamine agonists may be reduced while still producing the desired beneficial effects and this decrease in dose will result in a corresponding reduction of unwanted side effects.

In addition, clinical studies have shown that 23–52% of patients with Parkinson's disease have swallowing difficulties and many such patients tend to dribble. Accordingly, such fast-dispersing dosage forms have the further advantage that they will disintegrate rapidly in the mouth thereby minimizing the above problems as large volumes of water will not be co-administered. It is therefore anticipated that such fast-dispersing dosage forms will be easier for patients to take and easier for caregivers to administer.

One example of a fast-dispersing dosage form is described in U.S. Pat. No. 4,855,326 in which a melt spinnable carrier agent, such as sugar, is combined with an active ingredient and the resulting mixture spun into a "candy-floss" preparation. The spun "candy-floss" product is then compressed into a rapidly dispersing, highly porous solid dosage form.

U.S. Pat. No. 5,120,549 discloses a fast-dispersing matrix system which is prepared by first solidifying a matrix-forming system dispersed in a first solvent and subsequently contacting the solidified matrix with a second solvent that is substantially miscible with the first solvent at a temperature lower than the solidification point of the first solvent, the matrix-forming elements and active ingredient being substantially insoluble in the second solvent, whereby the first solvent is substantially removed resulting in a fast-dispersing matrix.

U.S. Pat. No. 5,079,018 discloses a fast-dispersing dosage form which comprises a porous skeletal structure of a water soluble, hydratable gel or foam forming material that has been hydrated with water, rigidified in the hydrated state with a rigidifying agent and dehydrated with a liquid organic solvent at a temperature of about 0° C. or below to leave spaces in place of hydration liquid.

Published International Application No. WO93/12769 (PCT/JP93/01631) describes fast-dispersing dosage forms of very low density formed by gelling, with agar, aqueous systems containing the matrix-forming elements and active ingredient, and then removing water by forced air or vacuum drying.

U.S. Pat. No. 5,298,261 discloses fast-dispersing dosage forms which comprise a partially collapsed matrix network that has been vacuum-dried above the collapse temperature of the matrix. However, the matrix is preferably at least partially dried below the equilibrium freezing point of the matrix.

Published International Application No. WO 91/04757 (PCT/US90/05206) discloses fast-dispersing dosage forms which contain an effervescent disintegration agent designed to effervesce on contact with saliva to provide rapid disintegration of the dosage form and dispersion of the active ingredient in the oral cavity.

U.S. Pat. No. 5,073,374 to McCarthy discloses a compressed tablet dosage form composed of 90–99% by weight of a water-soluble excipient (sucrose, lactose or sorbitol) and a bucally absorbable active agent. McCarthy also requires 1–3% by weight of a pharmaceutically acceptable lubricant such as a magnesium stearate or sodium dodecyl stearate which is added so that disintegration occurs from about 0.5 to 5 minutes after administration. In contrast, the dosage form according to the present invention does not include a lubricant. In fact, the presence of a lubricant would detrimentally impact upon the disintegration times of the present invention. Further, there is no mention or suggestion in McCarthy of sublimation, a required element in the presently claimed pharmaceutical dosage form.

U.S. Pat. No. 5,529,789 to Lo discloses a process dependent composition to achieve rapid dissolution utilizing a water-soluble, menthol-soluble component. After subliming menthol from the pharmaceutical composition, a solid, water-soluble polymer matrix remains. Lo teaches the use of a menthol-soluble polymer rather than a sugar as the soluble excipient.

SUMMARY OF THE INVENTION

The present invention is directed to a pharmaceutical composition for oral administration. In one embodiment, this dosage form is prepared from a composition that consists essentially of water, mannitol and gelatin at a concentration of up to 5% by weight as a carrier and as an active ingredient, a dopamine agonist. In another embodiment, the dosage form according to the present invention is a solid, unitary, fast-dispersing dosage form that comprises a network of the active ingredient and a water-soluble or water dispersible carrier which is inert towards the active ingredient. The network for the dosage form is obtained by subliming solvent from a composition in the solid state. That composition may consist essentially of the active ingredient and a solution of the carrier in a solvent. The dosage form according to the present invention will disintegrate completely within 1 to 30 seconds of being placed in the oral cavity.

Thus, there is disclosed a pharmaceutical composition for oral administration consisting essentially of gelatin at a concentration of up to 5% by weight as a carrier, water, and, as an active ingredient, a dopamine agonist, characterized in that the composition is in the form of a solid, unitary fast-dispersing dosage form consisting essentially of a network of the active ingredient and a carrier which is inert towards the active ingredient after subliming the water from the composition in the solid state. This dosage form completely disintegrates within 1 to 30 seconds of being placed in the oral cavity. essentially of a solvent, at least one dopamine agonist, at least one matrix forming agent and at least one agent selected from the group consisting of surfactants, preservatives, antioxidants, viscosity enhancers, coloring agents, flavoring agents, pH modifiers, sweeteners, anti-emetic agents, opioid antagonists and excipients. The solid, fast-dispersing dosage form completely disintegrates within 1–30 seconds of being placed in the oral cavity.

There is also disclosed a solid unitary dosage form that disintegrates within 1 to 30 seconds of being placed in the oral cavity obtainable by the process of dispersing at least one matrix forming agent with a solvent to prepare a dispersion/solution and adding to said dispersion/solution at least one dopamine agonist to prepare an agonist dispersion/solution. Added to said agonist dispersion solution is at least one agent selected from the group consisting of surfactants, preservatives, antioxidants, viscosity enhancers, coloring agents, flavoring agents, pH modifiers, sweeteners, anti-emetic agents, opioid antagonists and excipients to prepare a final dispersion. This final dispersion is then dispensed into preformed blister pockets and freeze dried in the blister pockets to obtain said unitary dosage form.

The preferred dopamine agonist for use in the present invention is apomorphine or a salt thereof. Compositions according to the present invention may further include an anti-emetic.

Further, the present invention is directed to a method for the treatment of Parkinson's disease which comprises orally administering to a patient, a therapeutically Further, the present invention is directed to a method for the treatment of Parkinson's disease which comprises orally administering to a patient, a therapeutically effective amount of the pharmaceutical composition according to the invention. The dopamine agonist may be selected from the group consisting of apomorphine, N-propylnoraporphine, bromocriptine, cabergoline, lisuride, metergoline, naxagolide, pergolide, piribedil, ripinirole, terguride and quinagolide, salts and mixtures thereof.

DETAILED DESCRIPTION OF THE INVENTION

The term "fast-dispersing dosage form" encompasses all the types of dosage forms that are prepared by subliming a solvent from a composition or mixture that is in the solid state. However, it is preferred that the fast-dispersing dosage form is of the type described in U.K. Patent No. 1,548,022, that is, a solid fast-dispersing dosage form comprising a network of the active ingredient and a water-soluble or water-dispersible carrier which is inert towards the active ingredient, the network having been obtained by subliming solvent from a composition in the solid state, that composition comprising the active ingredient and a solution or dispersion of the carrier in a solvent.

It is preferred that the dosage form of the invention disintegrates within 1 to 60 seconds, more preferably 1 to 30 seconds, especially 1 to 10 seconds and particularly 2 to 8 seconds, of being placed in the oral cavity.

In the case of the preferred type of fast-dispersing dosage form described above, the composition will preferably contain, in addition to the active ingredient, matrix forming agents or carriers and secondary components. Matrix forming agents or carriers suitable for use in the present invention include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other matrix forming agents or carriers suitable for use in the present invention include sugars such as mannitol, dextrose, lactose, galactose and trehalose; cyclic sugars such as cyclodextrin; inorganic salts such as sodium phosphate, sodium chloride and aluminum silicates; and amino acids having from 2 to 12 carbon atoms such as a glycine, L-alanine, L-aspartic acid, L-glutamic acid, L-hydroxyproline, L-isoleucine, L-leucine and L-phenylalanine.

One or more of these matrix forming agents can be combined to create a water-soluble or water dispersible carrier which is inert towards the active ingredient.

One or more matrix forming agents may be incorporated into the solution or suspension prior to solidification. In addition to forming the matrix, the matrix forming agent or carrier may aid in maintaining the suspension of any active ingredient within the solution or suspension. This is especially helpful in the case of active agents that are not sufficiently soluble in water and must, therefore, be suspended rather than dissolved.

Secondary components that do not materially affect the basic and novel characteristics of the inventive composition and dosage form include materials such as preservatives, antioxidants, surfactants, viscosity enhancers, coloring agents, flavoring agents, pH modifiers, sweeteners or taste-masking agents. Suitable coloring agents include red, black and yellow iron oxides and FD & C dyes such as FD & C Blue No. 2 and FD & C Red No. 40 available from Ellis & Everard. Suitable flavoring agents include mint, raspberry, licorice, orange, lemon, grapefruit, caramel, vanilla, cherry and grape flavors and combinations of these. Suitable pH modifiers include citric acid, tartaric acid, phosphoric acid, hydrochloric acid and maleic acid. Suitable sweeteners include aspartame, acesulfame K and thaumatic. Suitable taste-masking agents include sodium bicarbonate, ion-exchange resins, cyclodextrin inclusion compounds, adsorbates or microencapsulated actives.

It is preferred that the dopamine agonist is selected from 5,6,6a,7-tetrahydro-6-methyl-4H-dibenzo quinoline- 10; 11-diol (apomorphine); 5,6,6a,7-tetrahydro-6-propyl-4H-dibenzo quinoline- 10, 11-diol (N-propylnoraporphine); (5'α)-2-bromo- 12'-hydroxy-2'-(1-methylethyl)-5'-(2-methylpropyl) ergotaman-3', 6', 18-trione (bromocriptine); 1-((6-allylergolin-8β-yl) carbonyl)-1-[3-(dimethylamino) propyl]-3-ethylurea (cabergoline); N'-[(8α)-9, 10-didehydro-6-methylergolin-8-yl]-N,N-diethylurea (lisuride); [(8β)-1,6-dimethylergolin-8-yl] methyl]-carbamic acid phenylmethyl ester (metergoline); (4aR)-trans-3,4,4a,5,6, 10b-hexahydro-4-propyl-2H-naphth [1,2-b]- 1, 4-oxazin-9-ol (naxagolide); 8-[(methylthio) methyl]-6-propylergoline (pergolide); 2-[4-(1,3-benzodioxol-5-ylmethyl)-1-piperazinyl] pyrimidine (piribedil); 4-[2-(dipropylamino) ethyl] indolin-2-one (ropinirole); N,N-diethyl-N'-[8α)-6-methylergolin-8-yl] urea (terguride); and (±) -N,N-diethyl-N'-[(3R,4aR*,10aS*)-1,2,3,4,4a,5,10,10a-octahydro-6-hydroxy- 1-propylbenzo[g]quinolin-3-yl] sulphamide (quinagolide) salts thereof and mixtures thereof. More preferably, the dopamine agonist is apomorphine or a salt, preferably an acid-addition salt thereof, especially hydrochloride salt.

It is also preferred that the dopamine agonist is present in the composition in an amount from 0.05 to 100 mg, preferably 0.05 to 20 mg.

The precise quantity of active ingredient will depend on the dopamine agonist chosen. Preferred daily dose ranges for the dopamine agonists mentioned above are as follows:

| | | |
|---|---|---|
| Apomorphine | 1–150 mg | More preferably 10–60 mg |
| N-propylnoraporphine | 1–150 mg | More preferably 10–60 mg |
| Bromocriptine | 0.5–100 mg | More preferably 0.5–10 mg |
| Cabergoline | 0.05–2 mg | More preferably 0.2–0.6 mg |
| Lisuride | 0.05–5 mg | More preferably 0.05–1 mg |
| Metergoline | 4–20 mg | More preferably 4–8 mg |
| Naxagolide | 0.1–10 mg | More preferably 0.1–5 mg |
| Pergolide | 0.05–10 mg | More preferably 0.05–1 mg |
| Piribedil | 1–20 mg | More preferably 3–20 mg |
| Ropinirole | 0.25–20 mg | More preferably 2–10 mg |
| Terguride | 1.0–10 mg | More preferably 3–6 mg |
| Quinagolide | 0.1–5 mg | More preferably 0.1–1 mg |

Where a high daily dose is required, this may be administered in several units of smaller dosage size.

As mentioned above, dopamine agonists produce side effects such as nausea and vomiting. It is therefore preferred that the composition of the invention is administered in conjunction with an anti-emetic. The anti-emetic may be conveniently administered in the same composition as the dopamine agonist. In one preferred aspect, the composition of the invention as defined above therefore further includes an anti-emetic. Alternatively, the anti-emetic may be administered separately from the dopamine agonist by any of the usual oral or parenteral routes of administration, for instance, by tablets, capsules, suspensions, suppositories, infusions, injections, etc., at a suitable time which may be before, after or simultaneously with administration of the dopamine agonist. It is particularly preferred that the anti-emetic is formulated in a fast-dispersing dosage form of the type described above as it is envisaged that such a fast-dispersing dosage form of the anti-emetic would have many of the advantages associated with such formulations, such as increased bioavailability, dose reduction, ease of administration etc. as described above, although the precise advantages observed will depend on the nature of the anti-emetic chosen.

It is preferred that the anti-emetic is present in the composition in an amount of from 1 to 120 mg, more preferably 1–60 mg. However, the precise quantity of anti-emetic to be administered to the patient will depend on the anti-emetic that is selected. Suitable anti-emetics include peripheral dopamine antagonists, such as 5-chloro-1-[1 -[3-(2,3-dihydro-2-oxo-1H-benzimidazol-1-yl)propyl]-4-piperidinyl]-1, 3-dihydro-2H-benzimidazol-2-one (domperidone) benzimidazol-2-one (domperidone) and salts thereof, and serotonin (5-HT₃)receptor antagonists, such as endo-1-methyl-N-(9-methyl-9-azabicyclo[3.3.1]non-3-yl)-1H-indazole-3-carboxamide (granisetron); 1,2,3, 9-tetrahydro-9-methyl-3-[(2-methyl-1H-imidazol-1-yl) methyl]-4H-carbazol-4-one (ondansetron) and 1αH, 5αH-tropan-3α-yl indole-3-carboxylate (tropisetron) and salts thereof. Of these, domperidone is especially preferred.

Preferred daily dose ranges for the anti-emetics mentioned above are as follows:

| | | |
|---|---|---|
| Domperidone | 20–120 mg | More preferably 30–60 mg |
| Granisetron | 1–10 mg | More preferably 1–3 mg |
| Ondansetron | 4–32 mg | More preferably 4–8 mg |
| Tropisetron | 1–10 mg | More preferably 1–5 mg |

Where a high daily dose is required, this may be administered in several units of smaller dosage size.

Apomorphine is an opium alkaloid. Thus, as mentioned above, when apomorphine or another opium alkaloid or synthetic derivative is selected as the dopamine agonist, further side effects, such as sedation, respiratory depression, hypotension, bradycardia, sweating and yawning, will be produced in addition to nausea and vomiting. However, it has been found that all these side effects can be treated by administration of an opioid antagonist in conjunction with the opioid dopamine agonist. The opioid antagonist may be conveniently administered in the same composition as the dopamine agonist. Thus, in another preferred aspect, the composition of the invention as defined above further includes an opioid antagonist. Such a composition may also include an anti-emetic in addition to the dopamine agonist and opioid antagonist although this is not essential since the opioid antagonist also counteracts some of the emetic effects of the dopamine agonist. Alternatively, the opioid antagonist may be administered separately from the dopamine agonist by any of the usual oral or parenteral routes of administration at a suitable time which may be before, after or simultaneously with administration of the dopamine agonist. It is particularly preferred that the opioid antagonist is formulated in a fast-dispersing dosage form of the type described above as it is envisaged that such a fast-dispersing dosage form of the opioid antagonist would exhibit many of the advantages associated with such formulations, such as increased bioavailability, dose reduction, ease of administration etc. as described above, although the precise advantages observed will depend on the nature of the opioid antagonist chosen.

It is preferred that the opioid antagonist is present in the composition in an amount of from 0.5 to 100 mg, more preferably 0.5 to 50 mg. However, the precise quantity of opioid antagonist to be administered to the patient will depend on the opioid antagonist that is chosen. Suitable opioid antagonists include 4, 5-epoxy-3, 14-dihydroxy-17-(2-propenyl)morphinan-6-one (naloxone) and 17-(cyclopropylmethyl)-4, 5-epoxy-3,14-dihydroxymorphinan-6-one (naltrexone) and salts, particularly acid-addition salts and, especially, the hydrochloride, thereof The preferred daily dose range for naloxone is 0.25–10 mg, more preferably 0.5–2 mg, and for naltrexone is 10–100 mg, more preferably 25–50 mg. Where a high daily dose is required this may be administered in several units of smaller dose. According to another aspect of the invention there is provided a process for preparing any of the pharmaceutical compositions of the invention as described above which comprises bringing a carrier into association with the active ingredient and/or the anti-emetic and/or the opioid antagonist.

In a further aspect, the invention provides the use of a fast-dispersing dosage form designed to release active ingredient rapidly in the oral cavity to deliver a dopamine agonist. A method of administering a dopamine agonist to a patient which comprises introducing into the oral cavity of the patient a composition as previously defined is also provided.

As mentioned above, the composition of the invention can be used to combat the effects of Parkinson's disease. Accordingly, the invention also provides a composition as previously defined for use in the treatment of Parkinson's disease. A method of treating Parkinson's disease which comprises introducing into the oral cavity of a patient a therapeutically effective amount of a composition as previously defined is also provided.

In addition, dopamine agonists, especially apomorphine, can be used to predict the likely response to levodopa in patients with Parkinson's disease. Accordingly, the invention further provides a composition as previously defined for use in the evaluation of Parkinson's disease. A method of evaluating Parkinson's disease which comprises introducing into the oral cavity of a patient a selected amount of a composition as previously defined and determining the clinical effect of the composition on the patient is also provided.

In another aspect, the invention provides the use of a composition as previously defined for the manufacture of a medicament for the treatment and/or evaluation of Parkinson's disease.

As previously mentioned, it is envisaged that the dopamine agonist could be administered in conjunction with an anti-emetic and/or opioid antagonist, if appropriate, but that the anti-emetic and/or opioid antagonist could be administered by a variety of routes and the individual elements could be administered in a variety of sequences. According to another aspect of the invention there is therefore provided a kit for co-administration of a composition containing a dopamine agonist as previously defined and an anti-emetic and/or opioid antagonist. For instance, the kit may comprise at least one fast-dispersing unit dosage form of a dopamine agonist according to the invention, at least one unit dosage form of an anti-emetic and, if the dopamine agonist is an opium alkaloid, at least one unit dosage form of an opioid antagonist together with instructions for the administration of the unit dosage forms. In a preferred form of the kit, the anti-emetic is to be administered prior to the administration of the dopamine agonist. For ease of administration, it is further preferred that the anti-emetic and opioid antagonist, if present, be provided in the form of fast-dispersing dosage forms of the type previously defined. Accordingly, the kit may comprise a combination of fast-dispersing dosage forms as previously defined, preferably with instructions as to the sequence of administration. In a particularly preferred form, the kit may comprise a blister pack containing designated unit dosage forms of compositions as previously defined. Preferably, the sequence of administration of the designated unit dosage forms is marked on the blister pack. A particularly preferred kit comprises fast-dispersing dosage forms containing apomorphine and domperidone and/or naloxone.

According to another aspect of the invention there is provided a method of co-administering a dopamine agonist and an anti-emetic and/or opioid antagonist to a patient which comprises introducing into the oral cavity of the patient a composition containing a dopamine agonist as previously defined and administering an anti-emetic and/or opioid antagonist to the patient either orally or parenterally.

It is preferred that the anti-emetic and opioid antagonist, if present, are also provided in the form of fast-dispersing dosage forms of the type previously defined, either separately or in combination with the dopamine agonist, which may also be introduced into the oral cavity of the patient. The invention is further illustrated by the following examples.

EXAMPLE 1

Preparation of a Fast-dispersing Dosage Form of Apomorphine (a) Preparation of Apomorphine Hydrochloride 2.0% Dispersion Gelatin (792 g) and mannitol (594 g) were dispersed in a portion of purified water (16 kg) by mixing thoroughly in the bowl of a vacuum mixer. The mix was then heated to 40° C.±2° C. and homogenized for ten minutes. The mix was cooled down to room temperature (20–24° C.) When cooled the apomorphine hydrochloride (360 g) was added. The mix was homogenized to ensure dissolution of the drug. Citric acid (166.32 g) was added gradually with stirring, to adjust the solution pH to 3.0. The remaining water (87.68 g) was added to the mixer and the bulk mix homogenized to ensure dissolution was complete.

(b) Preparation of Apomorphine Hydrochloride 10 mg Units 500 mg of the apomorphine hydrochloride 2.0% dispersion, as formed in (a) above was dosed into each one of a series of pre-formed blister pockets having a pocket diameter of 16 mm. The blister laminate comprised 200 μm PVC coated with 40 g per square meter PVdC. The product was frozen immediately in a liquid nitrogen freeze tunnel. The frozen product was then stored below –20° C. for a minimum of 12 hours prior to freeze-drying in a freeze drier using a drying temperature of +10° C. and a chamber pressure of 0.5 mbar. The freeze dried units were then inspected for the presence of critical defects and the remainder of the batch sealed with lidding foil consisting of a paper/foil laminate (20 gm aluminum). Each blister was then coded with a batch number and overwrapped in a preformed sachet by placing the blister in the sachet and sealing the open end of the sachet completely. Each sachet was then labeled with the product name, batch number, date of manufacture and suppliers name.

Each dosage form or unit had the following composition:

| Ingredient | Weight (mg) | by weight of composition |
| --- | --- | --- |
| Purified water USP/EP* | 446.880 | 89.4 |
| Apomorphine HCl BP/EP | 10.000 | 2.0 |
| Gelatin EP/USNF | 22.000 | 4.4 |
| Mannitol EP/USP | 16.500 | 3.3 |
| Citric Acid EP/USP | 4.620 | 0.9 |

*Signifies removal during the lyophilization process

EXAMPLE 2

Comparative Pharmacokinetic Study

The objective of this study was to compare the bioavailability of apomorphine hydrochloride following administration by the oral route of a fast-dispersing dosage form prepared by the method of Example 1 and administration of a commercially available injectable formulation by the subcutaneous route (subcutaneous) to 12 healthy volunteers. The study was an open, randomized, comparative, 5-way cross-over pharmacokinetic study. Due to the emetic properties of apomorphine, subjects were pre-treated with the anti-emetic domperidone. Following 2 days of domperidone pre-treatment, subjects were randomized to receive the following apomorphine treatments over 5 consecutive days:

| | |
|---|---|
| 5 mg apomorphine | (half unit of Example 1) |
| 10 mg apomorphine | (one unit of Example 1) |
| 20 mg apomorphine | (two units of Example 1 administered simultaneously) |
| 2.5 mg subcutaneous injection | (Britajec ™) of apomorphine into the abdominal wall |
| 10 mg apomorphine | (one unit of Example 1) followed 5 minutes later by further 10 mg apomorphine (one unit of Example 1). |

Blood samples for pharmacokinetic analysis were taken pre-dose and at intervals for 6 hours after each dose of apomorphine. Assessment of the bioavailability of apomorphine was made using the pharmacokinetic parameter AUC (area under the plasma apomorphine concentration-time curve).

Doses of 5 mg, 10 mg and 20 mg of Example 1 produced dose-related increase in bioavailability as assessed by AUC (see Table I). Furthermore, giving two 10 mg doses 5 minutes apart resulted in an increase in bioavailability over the bioavailability of the 20 mg dose given at once.

TABLE I

The bioavailability of apomorphine given orally as Example 1 (5 mg to 20 mg), as two 10 mg doses 5 minutes apart and as a 2.5 mg subcutaneous injection. (Mean values)

| Dosage Group | AUC |
|---|---|
| 2.5 mg subcutaneous | 831.0 |
| 3 mg (Example 1) | 337.6 |
| 10 mg (Example 1) | 504.8 |
| 20 mg (Example 1) | 690.1 |
| 2 × 10 mg (Example 1) | 908.6 |

In Example 2 it was shown that the overall absorption of apomorphine, when administered from a rapidly disintegrating dosage form, was increased when the 20 mg dose was administered as two 10 mg units taken five minutes apart rather than taking two 10 mg units simultaneously. It is believed that the observed enhanced absorption may be due to the effect of the formulation on the pH of the saliva of the mouth, in which the drug must be dissolved before it can be absorbed pre-gastrically.

Apomorphine is a basic drug which is known to exhibit optimal chemical stability in an acidic environment. Therefore formulations of apomorphine normally include excipients such as citric acid, tartaric acid or maleic acid to maximize chemical stability. These excipients would be expected to cause a fall in the salivary pH which may affect the absorption of the drug. This effect is surprisingly minimized by administering the dose over a period of time.

According to another aspect of the invention there is therefore provided a pharmaceutical product comprising a therapeutic dose of a pharmaceutical composition containing a dopamine agonist as previously defined in which the therapeutic dose of the composition is divided into at least two portions and the pharmaceutical product additionally comprises instructions to administer said at least two portions sequentially with a specified time period between administration of each portion.

The invention also provides a method of administering to a patient a pharmaceutical product comprising a therapeutic dose of a pharmaceutical composition containing a dopamine agonist as previously defined in which said therapeutic dose of the composition is divided into at least two portions which method comprises introducing the at least two portions sequentially into the oral cavity of the patient with a specified time period between administration of each portion.

Preferably, the specified time period between administration of each portion is from 2 to 15 minutes, more preferably from 5 to 10 minutes. It is also preferred that the instructions for administration of the at least two portions are marked on a pack containing the portions. Most preferably, the at least two portions are contained in a blister pack and the instructions are preferably marked on the blister pack.

In a further aspect, the invention provides a kit for the administration of a composition containing a dopamine agonist as previously defined which comprises at least first and second designated unit dosage forms of the composition and instructions specifying a time sequence for the sequential administration of the at least first and second designated unit dosage forms.

The invention also provides a method of administering to a patient a composition containing a dopamine agonist as previously defined comprising at least first and second designated unit dosage forms of the composition which method comprises sequentially introducing said at least first and second designated unit dosage forms into the oral cavity of the patient in accordance with a specified time sequence.

It is preferred that the time sequence is such that a period of from 2 to 15 minutes, more preferably from 5 to 10 minutes, is required to elapse between administration of the first and second designated unit dosage forms. Preferably, the instructions specifying the time sequence for sequential administration of the at least first and second designated unit dosage forms are marked on a pack containing the designated unit dosage forms. It is particularly preferred that the designated unit dosage forms are contained in a blister pack. Preferably, the instructions are marked on the blister pack.

It is especially preferred that the dopamine agonist utilized in the pharmaceutical product or kit as previously defined is apomorphine, N-propylnoraporphine or a salt thereof. Preferably, each portion or designated unit dosage form contains from 2.5 to 20 mg, more preferably from 5 to 15 mg and especially 10 mg, of apomorphine or a salt thereof.

A further aspect of this discovery that absorption of apomorphine can be enhanced by administering the dose over a period of time. In this way, the pH of the saliva can be maintained within the normal physiological range at the time of taking the apomorphine formulation. Co-administration of an antacid formulation will also be effective. This could be either a specially prepared formulation or a commercially available tablet or liquid formulation such as Rennie™, Settlers™, Bisodol™, Aludrox™, Asilone™ or Remegel™. The antacid would react directly with the acid excipient and prevent the fall in pH of the saliva which is believed to reduce the overall absorption of apomorphine from the pre-gastric region of the gastrointestinal tract.

According to a further aspect of the invention there is therefore provided a pharmaceutical product or kit as previously defined which further includes an antacid.

The invention also provides a method of administering a dopamine agonist, a pharmaceutical product or designated unit dosage forms containing a dopamine agonist as previously defined, a method of co-administering a dopamine agonist and an anti-emetic and/or opioid antagonist as previously defined and a method of treating and/or evaluating Parkinson's disease as previously defined all of which comprise the further step of introducing an antacid into the oral cavity of the patient. The antacid may be administered just before or after or simultaneously with administration of the dopamine agonist. An antacid for use in enhancing pre-gastric absorption of the active ingredient from a composition containing a dopamine agonist as previously defined is also provided.

EXAMPLE 3

Pre-gastric Absorption Study

The objective of this study was to compare the bioavailability of apomorphine hydrochloride 10 mg following administration by the oral route as a fast-dispersing dosage form (Example 1) placed into the mouth and allowed to disperse and when encapsulated in a hard gelatin capsule and swallowed whole. The study was an open, randomized, comparative, 2-way cross-over pharmacokinetic study with 6 volunteers.

Due to the emetic properties of apomorphine, subjects were pre-treated with the anti-emetic domperidone. Following 2 days of domperidone pre-treatment, subjects were randomized to receive the following apomorphine treatments over 2 consecutive days:

10 mg apomorphine (Example 1)

10 mg apomorphine encapsulated into a hard gelatin capsule.

Blood samples for pharmacokinetic analysis were taken pre-dose and at intervals for 6 hours after each dose of apomorphine. Assessment of the bioavailability of apomorphine was made using the pharmacokinetic parameter AUC.

The doses of 10 mg (Example 1) produced a plasma profile similar to that seen in Example 2 (see Table 1). However, the same formulation when given encapsulated in a hard gelatin capsule gave a significantly reduced plasma profile. This was seen clearly in the pharmacokinetic parameter AUC, which indicated significantly reduced absorption in the hard gelatin capsule group (Table II).

These results support the concept that apomorphine is absorbed pre-gastrically from the fast-dispersing dosage forms of Example 1 when placed into the mouth since, when the same formulation was encapsulated (which would prevent pre-gastric absorption), the amount of apomorphine detected in plasma was significantly reduced.

TABLE II

The bioavailability of apomorphine given orally in the form of Example 1 (10 mg) and 10 mg encapsulated in a hard gelatin capsule (mean values).

| Dosage Group | AUC |
|---|---|
| 10 mg (Example 1) | 402.2 |
| 10 mg in a hard gelatin capsule | 92.3 |

The following examples further exemplify formulations which can be prepared using the process described in Example 1:

EXAMPLE 4

| Ingredient | Weight (mg) | % by weight of composition |
|---|---|---|
| Purified Water EP/USP* | 438.500 | 87.70 |
| Apomorphine HCl BP/EP | 10.000 | 2.00 |
| Gelatin EP/USNF | 25.000 | 5.00 |
| Mannitol EP/USP | 20.000 | 4.00 |
| Citric Acid EP/USP | 1.500 | 0.30 |
| Aspartame EP/USNF | 2.500 | 0.50 |
| Peppermint Flavor | 2.500 | 0.50 |
| TOTAL | 500.00 | 100.00 |

*signifies removal during lyophilization process

EXAMPLE 5

| Ingredient | Weight (mg) | % by weight of composition |
|---|---|---|
| Purified Water EP/USP* | 215.000 | 86.00 |
| Apomorphine HCl BP/EP | 10.000 | 4.00 |
| Gelatin EP/USNF | 11.500 | 4.60 |
| Mannitol EP/USP | 10.000 | 4.00 |
| Citric Acid EP/USP | 1.500 | 0.60 |
| Aspartame EP/USNF | 2.000 | 0.80 |
| TOTAL | 250.000 | 100.00 |

*signifies removal during lyophilization process

EXAMPLE 6

| Ingredient | Weight (mg) | % by weight of composition |
|---|---|---|
| Purified Water EP/USP* | 441.000 | 88.20 |
| Apomorphine HCl BP/EP | 10.000 | 2.00 |
| Gelatin EP/USNF | 25.000 | 5.00 |
| Mannitol EP/USP | 20.000 | 4.00 |
| Citric Acid EP/USP | 1.500 | 0.30 |
| Aspartame EP/USNF | 2.500 | 0.50 |
| TOTAL | 500.000 | 100.00 |

*signifies removal during lyophilization process

EXAMPLE 7

| Ingredient | Weight (mg) | % by weight of composition |
|---|---|---|
| Purified Water EP/USP* | 425.000 | 85.00 |
| Apomorphine HCl BP/EP | 10.000 | 2.00 |
| Domperidone | 20.000 | 4.00 |
| Gelatin EP/USNF | 20.000 | 4.00 |
| Mannitol EP/USP | 15.000 | 3.00 |
| Glycine USP | 5.000 | 1.00 |
| Aspartame EP/USNF | 2.500 | 0.50 |
| Peppermint Flavor | 2.500 | 0.50 |
| TOTAL | 500.000 | 100.00 |

*signifies removal during lyophilization process

EXAMPLE 8

| Ingredient | Weight (mg) | % by weight of composition |
|---|---|---|
| Purified Water EP/USP* | 138.2500 | 92.1667 |
| Lisuride Maleate | 0.2000 | 0.1333 |
| Gelatin EP/USNF | 6.0000 | 4.0000 |
| Mannitol EP/USP | 4.5000 | 3.0000 |
| Aspartame EP/USNF | 0.3000 | 0.2000 |
| Cherry Flavor | 0.7500 | 1.5000 |
| TOTAL | 150.000 | 100.0000 |

*signifies removal during lyophilization process

EXAMPLE 9

| Ingredient | Weight (mg) | % by weight of composition |
|---|---|---|
| Purified Water EP/USP* | 138.9500 | 92.6333 |
| Pergolide Mesylate | 0.2500 | 0.1667 |
| Gelatin EP/USNF | 6.0000 | 4.0000 |
| Mannitol EP/USP | 4.5000 | 3.0000 |
| Aspartame EP/USNF | 0.3000 | 0.2000 |
| TOTAL | 150.000 | 100.0000 |

*signifies removal during lyophilization process

EXAMPLE 10

| Ingredient | Weight (mg) | % by weight of composition |
|---|---|---|
| Purified Water EP/USP* | 226.250 | 90.50 |
| Bromocriptine Mesylate | 2.500 | 1.00 |
| Gelatin EP/USNF | 10.000 | 4.00 |
| Mannitol EP/USP | 7.500 | 3.00 |
| Aspartame EP/USNF | 1.250 | 0.50 |
| Cherry Flavor | 1.250 | 0.50 |
| Peppermint Flavor | 1.250 | 0.50 |
| TOTAL | 250.000 | 100.00 |

*signifies removal during lyophilization process

EXAMPLE 11

| Ingredient | Weight (mg) | % by weight of composition |
|---|---|---|
| Purified Water EP/USP* | 137.750 | 91.8333 |
| Ropinrole | 1.000 | 0.6667 |
| Gelatin EP/USNF | 6.000 | 4.0000 |
| Mannitol EP/USP | 4.500 | 3.0000 |
| Aspartame EP/USNF | 2.500 | 0.50 |
| TOTAL | 150.000 | 100.0000 |

*signifies removal during lyophilization process

EXAMPLE 12

| Ingredient | Weight (mg) | % by weight of composition |
|---|---|---|
| Purified Water EP/USP* | 431.500 | 86.30 |
| Apomorphine HCl BP/EP | 10.000 | 2.00 |
| Naloxone HCl BP/EP | 10.000 | 2.00 |
| Gelatin EP/USNF | 20.500 | 4.10 |
| Mannitol EP/USP | 15.000 | 3.00 |
| Citric Acid EP/USP | 1.500 | 0.30 |
| Aspartame EP/USNF | 3.000 | 0.60 |
| Grapefruit Flavor | 1.000 | 0.20 |
| Glycine USP | 7.500 | 1.50 |
| TOTAL | 500.000 | 100.00 |

*signifies removal during lyophilization process

EXAMPLE 13

| Ingredient | Weight (mg) | % by weight of composition |
|---|---|---|
| Purified Water EP/USP* | 413.000 | 82.60 |
| Apomorphine HCl BP/EP | 10.000 | 2.00 |
| Naltrexone HCl | 25.000 | 5.00 |
| Gelatin EP/USNF | 22.500 | 4.50 |
| Mannitol EP/USP | 15.000 | 3.00 |
| Citric Acid EP/USP | 2.500 | 0.50 |
| Aspartame EP/USNF | 5.000 | 1.00 |
| Raspberry Flavor | 2.000 | 0.40 |
| Glycine USP | 5.000 | 1.00 |
| TOTAL | 500.000 | 100.00 |

*signifies removal during lyophilization process

EXAMPLE 14

| Ingredient | Weight (mg) | % by weight of composition |
|---|---|---|
| Purified Water EP/USP* | 397.250 | 79.45 |
| Apomorphine HCl BP/EP | 20.000 | 4.00 |
| Naloxone HCl BP/EP | 10.000 | 2.00 |
| Domperidone | 20.000 | 4.00 |
| Gelatin EP/USNF | 22.500 | 4.50 |
| Mannitol EP/USP | 17.500 | 3.50 |
| Citric Acid EP/USP | 1.500 | 0.30 |
| Lemon Lime Flavor | 2.500 | 0.50 |
| Glycine USP | 5.000 | 1.00 |
| Aspartame EP/USNF | 3.750 | 0.75 |
| TOTAL | 500.000 | 100.00 |

*signifies removal during lyophilization process

EXAMPLE 15

| Ingredient | Weight (mg) | % by weight of composition |
|---|---|---|
| Purified Water EP/USP* | 219.008 | 87.60 |
| Apomorphine HCl BP/EP | 5.000 | 2.00 |
| Granisetron HCl | 1.117 | 0.45 |
| Gelatin EP/USNF | 10.625 | 4.25 |
| Mannitol EP/USP | 7.500 | 3.00 |

-continued

| Ingredient | Weight (mg) | % by weight of composition |
|---|---|---|
| Citric Acid EP/USP | 1.500 | 0.60 |
| Mint Flavor | 1.500 | 0.60 |
| Glycine USP | 1.250 | 0.50 |
| Aspartame EP/USNF | 2.500 | 1.00 |
| TOTAL | 250.000 | 100.00 |

*signifies removal during lyophilization process

Industrial Applicability

The medical community is constantly in search of improved methods and compositions for treating numerous disorders. Parkinson's disease is an especially difficult disease to treat due to the physical condition of the patient. The present invention supplies a novel way of administering dopamine agonists, such as apomorphine, which is easy for the patient to accomplish therefore reducing the need for supervision of administration. Further, the dosage form according to the invention bypasses the first pass metabolism in the liver thereby reducing the total dose.

Further, the present invention has discovered that such dispersing dosage forms promote pre-gastric absorption of the active ingredient. Dopamine agonists absorbed by pre-gastric absorption pass straight into the systemic circulatory system thereby avoiding first pass metabolism in the liver.

While a detailed description and certain preferred embodiments of the invention have been provided above, the present invention is not limited thereto, but rather is defined in the following claims.

We claim:

1. A pharmaceutical composition for oral administration consisting essentially of gelatin at a concentration of up to 5% by weight as a carrier, water, and, as an active ingredient, apomorphine or a salt thereof, characterized in that the composition is in the form of a solid, unitary fast-dispersing dosage form consisting essentially of a network of the active ingredient and the carrier which is inert towards the active ingredient after subliming said water from said composition in the solid state, and, wherein said dosage form completely disintegrates within 1 to 30 seconds of being placed in the oral cavity.

2. The pharmaceutical composition according to claim 1 comprising at least one additional carrier.

3. The composition according to claim 1 which additionally comprises at least one agent selected from the group consisting of anti-emetic agents, opioid antagonists, excipients and flavoring agents.

4. A method for the treatment of Parkinson's disease consisting essentially of orally administering to a patient a therapeutically effective amount of a composition according to claim 1.

5. The method according to claim 4 wherein said composition additionally comprises at least one agent selected from the group comprising anti-emetic agents, opioid antagonists, excipients and flavoring agents.

6. A method for the treatment of Parkinson's disease consisting essentially of orally administering to a patient a therapeutically effective amount of a composition according to claim 2.

7. The method according to claim 4 wherein said composition comprises at least one additional carrier.

8. A solid, fast dispersing dosage form obtained by subliming a solvent from a composition in the solid state, that composition consisting essentially of:

(a) water;
(b) at least one dopamine agonist selected from the group consisting of apomorphine, N-propanoraporphine, bromocriptine, cabergoline, lisoride, metergoline, naxagolide, pergolide, piribedil, ripinerole, terguride and quinagolide, salts and mixtures thereof;
(c) at least one matrix forming agent; and
(d) at least one agent selected from the group consisting of surfactants, preservatives, antioxidants, viscosity enhancers, coloring agents, flavoring agents, pH modifiers, sweeteners, anti-emetic agents, opioid antagonists and excipients; and wherein said solid, fast-dispersing dosage form completely disintegrates within 1–30 seconds of being placed in the oral cavity.

9. The solid fast dispersing dosage form according to claim 8 wherein said composition consists essentially of:

(a) water;
(b) apomorphine HCl;
(c) gelatin;
(d) mannitol; and
(e) citric acid.

10. The solid, fast-dispersing dosage form according to claim 9 wherein said composition additionally comprises a sweetening agent.

11. The solid, fast-dispersing dosage form according to claim 10 wherein said composition additionally comprises a flavoring agent.

12. The solid, fast-dispersing dosage form according to claim 11 wherein said composition additionally comprises glycine.

13. The solid, fast-dispersing dosage form according to claim 9 wherein said composition additionally comprises at least one agent selected from the group consisting of anti-emetic agents, opioid antagonists, excipients and flavoring agents.

14. A solid, unitary dosage form that disintegrates within 1 to 30 seconds of being placed in the oral cavity obtainable by the process of:

(a) dispersing at least one matrix forming agent with water to prepare a dispersion/solution;
(b) adding to said dispersion/solution at least one dopamine agonist to prepare an agonist dispersion/solution;
(c) adding to said agonist dispersion/solution at least one agent selected from the group consisting of surfactants, preservatives, antioxidants, viscosity enhancers, coloring agents, flavoring agents, pH modifiers, sweeteners, anti-emetic agents, opioid antagonists and excipients to prepare a final dispersion;
(d) dispensing the final dispersion into pre-formed blister pockets and freezing the final dispersion in said blister pockets to form frozen final dispersions; and
(e) freeze-drying in a freeze dryer said frozen final dispersions to obtain said unitary dosage form.

15. The solid, unitary dosage form according to claim 14 wherein said final dispersion comprises:

(a) no more than 5% by weight gelatin;
(b) apomorphine hydrochloride;
(c) mannitol; and
(d) citric acid.

* * * * *